United States Patent [19]

Kos et al.

[11] Patent Number: 5,686,638

[45] Date of Patent: Nov. 11, 1997

US005686638A

[54] PROCESS FOR THE PREPARATION OF MONO- OR DICARBOXYLIC ACIDS FROM ALDEHYDES, FROM THEIR FULL ACETALS OR HEMIACETALS OR FROM MIXTURES THEREOF

[75] Inventors: Carlo Kos, Leonding; Manfred Schöftner; Johann Friedhuber, both of Linz, all of Austria

[73] Assignee: DSM Chemie Linz GmbH, Linz, Austria

[21] Appl. No.: 523,372

[22] Filed: Sep. 5, 1995

[30] Foreign Application Priority Data

Sep. 6, 1994 [AT] Austria ............................ 1701/94

[51] Int. Cl.⁶ ............................ C07C 51/16; C07C 51/21; C07C 51/34
[52] U.S. Cl. ............................ 554/134; 554/134; 562/407; 562/408; 562/523; 562/531
[58] Field of Search ................ 554/132, 134; 562/407, 408, 523, 531

[56] References Cited

U.S. PATENT DOCUMENTS

| | | | |
|---|---|---|---|
| 2,959,613 | 11/1960 | Whitfield | 562/531 |
| 3,441,604 | 4/1969 | Baylis et al. | |
| 4,285,875 | 8/1981 | Cornils et al. | |
| 4,287,130 | 9/1981 | Dohm et al. | |
| 4,709,088 | 11/1987 | Hirose et al. | 562/418 |
| 4,733,007 | 3/1988 | Andrade et al. | |
| 4,733,008 | 3/1988 | Andrade et al. | |
| 4,791,228 | 12/1988 | Siclari et al. | 562/531 |
| 5,310,944 | 5/1994 | Kawaki et al. | |

FOREIGN PATENT DOCUMENTS

| | | |
|---|---|---|
| 15 18 945 | 1/1974 | Germany. |
| 29 31 154 | 8/1985 | Germany. |
| 36 28 662 | 3/1988 | Germany. |
| 40 00 163 | 1/1990 | Germany. |
| 4-243850 | 8/1992 | Japan. |
| 10 41 695 | 9/1966 | United Kingdom. |

OTHER PUBLICATIONS

Canadian Application No. 115: 135523m, "Process for Preparation of α,ω–alkanedioic acids by sequential perioxidation, reduction, and oxidation of cycloalkenes", Chemical Abstracts, vol. 115, 1991 p. 922.

*Primary Examiner*—Gary Geist
*Assistant Examiner*—Deborah D. Carr
*Attorney, Agent, or Firm*—Wenderoth, Lind & Ponack

[57] ABSTRACT

Process for the preparation of aliphatic or aromatic mono- or dicarboxylic acids of 4 to 22 carbon atoms by oxidation of the corresponding aldehydes having the same number of carbon atoms in a carboxylic acid from the group consisting of formic acid, acetic acid, and propionic acid or in a carboxylic acid/water mixture at a temperature of 50°–130° C. and at 1 to 25 bar and in the presence of an oxidizing agent.

11 Claims, No Drawings

PROCESS FOR THE PREPARATION OF MONO- OR DICARBOXYLIC ACIDS FROM ALDEHYDES, FROM THEIR FULL ACETALS OR HEMIACETALS OR FROM MIXTURES THEREOF

Mono- and dicarboxylic acids, especially alpha,omega-alkanedicarboxylic acids, are valuable precursors in the chemical industry and are used, for example, in the production of pharmaceuticals, cosmetics, lubricants and the like. The literature therefore reveals a large number of preparation options for mono- and dicarboxylic acids. For example, GB 2,034,310 describes the oxidation of aldehyde acids or dialdehydes in acidic solution and in the presence of a cobalt salt and/or an iron salt catalyst. GB 1,539,573 likewise requires a catalyst in order to oxidize aldehyde acids to the corresponding dicarboxylic acids. The disadvantage of all the hitherto described oxidations in acidic solution, however, is a need for a catalyst which must be removed from the reaction mixture once reaction has taken place. Processes which are carried out without the addition of catalyst are likewise known but have the disadvantage that the oxidation takes place in aprotic solvents, for instance chlorobenzene. A further disadvantage of these processes is that the aldehydes must not contain any acetal.

The object of the present invention was accordingly to find a process which provides mono- and dicarboxylic acids in high yield and purity without the use of a catalyst and without using aprotic solvent, where the precursors may also contain acetal.

Accordingly, the present invention provides a process for the preparation of aliphatic or aromatic mono- or dicarboxylic acids of 4–22 carbon atoms by oxidation of the corresponding aldehydes having the same number of carbon atoms, which comprises carrying out the oxidation in a carboxylic acid from the group consisting of formic acid, acetic acid and propionic acid, or in a carboxylic acid/water mixture, at a temperature of 50°–130° C and at 1–25 bar in the presence of an oxidizing agent. By the process of the invention, mono- or dicarboxylic acids are obtained by oxidation of the corresponding aldehydes. Suitable aldehydes in this context are an aldehyde itself, its full acetal or hemiacetal, or a mixture of aldehyde and its hemlaterals and/or full acetals. Suitable mixtures of aldehyde and acetals may contain 1–99% aldehyde and, respectively, 1–99% acetal. The aldehydes employed may therefore either be aliphatic or aromatic aldehydes having in each case one or two aldehyde groups or hemiacetal or full acetal groups. An aliphatic aldehyde is a straight-chain, branched or cyclic mono- or dialdehyde of 4 to 22 carbon atoms, preferably 6 to 15 carbon atoms, where the alkyl chains may be unsubstituted or substituted by groups which are inert under the reaction conditions. Examples of such inert groups are aryl groups, such as naphthyl or phenyl which is unsubstituted or substituted by alkyl which is preferably of 1 to 6, particularly preferably 1 to 4, carbon atoms, such as methyl, ethyl, isopropyl, butyl, neopentyl or hexol, or by alkoxy, preferably of 1 to 6, particularly preferably 1 to 4, carbon atoms, such as methoxy, ethoxy, butoxy, isopentyloxy or hexyloxy groups, or are phenyl or naphthyl groups which are substituted by halogen, or are alkoxy groups, preferably those of 1 to 6 carbon atoms. Further examples of groups which are inert under the reaction conditions are ester groups, preferably with 1–4 carbon atoms in the ester moiety.

Aromatic aldehydes are aldehydes in which one or two aldehyde groups are bonded directly to an aromatic carbon atom, for example in a phenyl, naphthyl or pyridyl group, such as benzaldehyde, phthalaldehyde, naphthylaidehyde, pyridinaldehyde or pyridinedialdehydes. It is preferred to employ unsubstituted, aliphatic mono- and dialdehydes, especially dialdehydes, of 4 to 22 carbon atoms. A large number of processes are known for the preparation of aldehydes. According to U.S. Pat. No. 4,607,126 or U.S. Pat. No. 4,769,464, aldehydes or dialdehydes can be prepared on an industrial scale in a convenient manner, for example by ozonolysis and reduction of olefinic double bonds.

To carry out the reaction according to U.S. Pat. No. 4,769,464 for the preparation of the aldehydes, an appropriate chemical compound having at least one olefinic double bond is dissolved in an organic solvent in which it is readily soluble, for example in a lower aliphatic alcohol, preferably methanol, and the solution is treated with the equivalent quantity of ozone. Ozonization is carried out at temperatures of from about −30° to 0° C., preferably from about −20° to 0° C.

The catalytic hydrogenation of the ozonolysis products which follows on from ozonization is carried out in dilute solution, said hydrogenation preferably being carried out while observing a controlled peroxide content of not more than 0.1 mol/l. For this purpose, a suspension of the catalyst in the solvent is introduced, together with hydrogen, as initial charge, and the ozonolysis solution is fed in continuously. Keeping the peroxide content of the reaction medium low in this way avoids poisoning and a loss of activity of the catalyst.

The hydrogenation is carried out under conditions which include virtually atmospheric pressure, i.e. pressures of 1 to 3 bar, which are customarily employed in order to prevent the penetration of air into the hydrogenation reactor. The reaction temperature during hydrogenation is from about 20° to 40° C. The pH during the hydrogenation is kept within a range from 2 to 7. Since during the hydrogenation small amounts of acidic by-products may be formed, the pH may if desired be maintained within the desired range by addition of a base, preferably dilute sodium hydroxide or potassium hydroxide solution. Depending on the pH conditions, this reaction gives rise to aldehydes, their hemiacetals, their full acetals or mixtures thereof. In order to isolate the aldehydes, the catalyst is filtered off and the solvent is removed. Aldehydes which can be prepared by the described process are preferably employed in the process according to the invention.

The appropriate aldehyde is oxidized in a carboxylic acid as diluent or in a carboxylic acid/water mixture, using an oxidizing agent, to the desired mono- or dicarboxylic acid. Carboxylic acids suitable as diluents in this case are formic acid, acetic acid, propionic acid and the like. It is preferred to employ acetic acid as solvent. The carboxylic acids can be used either alone or as a mixture with water. It is preferred to use the carboxylic acids as a mixture with water, in which case the proportion of water can be about 0.1–25% by volume, preferably 5–15% by volume. The concentration of aldehydes in the solution is of little importance for the process of the invention. In general, the aldehyde concentrations used are as high as possible in order to save on solvent, although the concentration should not be so high that the aldehydes or the carboxylic acids formed precipitate from the reaction solution at the reaction temperature. The oxidizing agent used is oxygen or air, preferably oxygen. The oxidation is preferably carried out under pressure, with pressures of from 1 to 25 bar, preferably from 8 to 25 bar, being employed. The reaction temperature is from about 50° to 130° C., preferably 60° to 90° C. After the end of the reaction the reaction solution is cooled, preferably to 0°–35°

C., and worked up accordingly depending on the reaction product. For example, thermally stable monocarboxylic acids are separated by distillation, whereas thermally unstable monocarboxylic acids, on the other hand, are—if not soluble in water—isolated by washing the solvent out of the reaction mixture with water. Dicarboxylic acids are for example isolated, provided they are poorly soluble or insoluble in the solvent under cold conditions, at 0°–35° C., are isolated by crystallization and subsequent separation of the solids. The mother liquor obtained in this case can be topped up with the aldehyde component and water and then recycled directly to the oxidation process. The carboxylic acids isolated in this way may, if desired, be purified additionally by conventional methods, such as recrystallization distillation, or chromatographic methods. The process according to the invention can be carried out either batchwise or continuously.

In a preferred embodiment of the process of the invention, aliphatic and aromatic mono- or dicarboxylic acids of 4 to 22 carbon atoms are prepared by reacting a corresponding chemical compound having at least one olefinic double bond with ozone in the presence of a solvent, subjecting the peroxide solution formed to catalytic hydrogenation, and then oxidizing the aldehyde, after separating off the solvent and the catalyst, in the presence of a carboxylic acid from the group consisting of formic acid, acetic acid and propionic acid, or of a carboxylic acid/water mixture, without a catalyst, to give the desired mono- or dicarboxylic acid.

In this context, the ozonization and subsequent hydrogenation is preferably carried out by the method described in U.S. Pat. No. 4,769,464, and the oxidation is carried out under the conditions indicated above. Suitable chemical compounds having at least one olefinic double bond in this context are those compounds which lead to the aldehydes indicated above. Examples thereof are straight-chain, branched or cyclic ($C_4$–$C_{22}$) alkenes having at least one olefinic double bond, which may if desired be substituted by the groups which are inert under the reaction conditions and which have already been mentioned, examples of the alkenes being butene, pentene, hexene, isoprene, isobutene, isooctene, butadiene, octadiene, hexadecene, cyclohexene, cyclooctadiene, cyclooctene, cyclododecene, cyclododecatriene, terpenes or aromatic compounds having at least one olefinic double bond, for example styrenes, divinylbenzenes, diisopropenylbenzene, naphthylstyrenes or diphenylethylenes.

By the process of the invention, mono- and dicarboxylic acids are obtained in high purity and with outstanding yields. In general, yields of 90–98% are obtained without substantial waste products or waste waters and environmentally polluting waste gases. The mono- and dicarboxylic acids are obtained with at least 95% purity, and usually a purity of more than 98%, so that further purification of the end product is in most cases unnecessary.

EXAMPLE 1

Octanedioic acid 110.2 g (1 mol) of cyclooctene (purity 95%) were dissolved in 1500 ml of methanol, the solution was cooled to –20° C., and an $O_2/O_3$ mixture containing 4% by weight of ozone was passed in until 1 mol of ozone had been introduced into the solution. Subsequently, the ozonization solution obtained was fed continuously via a metering vessel into a hydrogenation reactor in which 2 g of Pd catalyst (Lindlar) had been placed and which was filled with hydrogen, at a rate such that the peroxide content did not exceed 0.02 mol/l. With vigorous stirring and addition of hydrogen, hydrogenation was carried out until peroxide sampling gave a negative result.

The catalyst was removed from the hydrogenation solution by filtration, the solvent was removed in vacuo and the residue was dissolved in 90% strength acetic acid so that the concentration of the aldehyde was 1 mol/l of solution. The solution was oxidized with oxygen at a pressure of 10 bar and at a temperature of 80° C. in an autoclave. After the end of the reaction the autoclave was let down and the solution was cooled to 15°–20° C. The precipitate formed was filtered off and dried in vacuo, at 20 mbar, at 80° C. The mother liquor was brought to the required concentration with water, solvent and crude aldehyde and recirculated to the oxidation stage. In this way, 125–152 g of octanedioic acid were obtained per cycle with a purity>98%.

EXAMPLE 2

Octanedioic acid

In analogy to Example 1, 108.18 g (1 mol) of cyclooctadiene (purity 95%) were supplied with ozone until 0.5 mol of ozone had been introduced into the solution, and the resulting ozonization solution was hydrogenated as in Example 1.

The hydrogenation solution thus obtained contained octanedial and its acetal.

The oxidation of the aldehyde/acetal mixture was carried out in analogy to Example 1. In this way, 125 g of octanedioic acid per cycle were obtained with a purity of 96%.

EXAMPLE 3

Dodecanedioic acid

In analogy to Example 1, 166.4 g (1 mol) of cyclododecene (purity 95%) were ozonized to dodecanedial which was subsequently subjected to catalytic hydrogenation. The oxidation of dodecanedial was carried out likewise as in Example 1. 220 g of dodecanedioic acid per cycle were obtained with a purity of 98%.

EXAMPLE 4

Dodecanedioic acid 162.3 g (1 mol) of cyclododecatriene (purity 95%) were dissolved in 1500 ml of methanol, the solution was cooled to –20° C., and an $O_3/O_2$ mixture containing 4% by weight of $O_3$ was passed in until 0.33 mol of ozone had been introduced into the solution. The hydrogenation solution obtained as in Example 1 contained dodecanedial and its acetals. Cyclododecane formed was extracted from the acetic acid solution using petroleum ether prior to the oxidation.

The oxidation of the aldehyde/acetal mixture was carried out as in Example 1 at 15 bar. 183 g of dodecanedioic acid per cycle were obtained with a purity of 98%.

EXAMPLE 5

Tridecanedioic acid 338.58 g (1 mol) of erucic acid (purity 95%) were ozonized in analogy to Example 1 and then hydrogenation was carried out. The hydrogenation solution obtained in this way contained nonanal and tridecanealdehyde acid and was divided by distillation. For oxidation, the corresponding aldehyde fraction was employed and was oxidized at 14 bar in analogy to Example 1. 185 g of tridecanedioic acid per cycle were obtained with a purity of 95%.

EXAMPLE 6

Perlagonic acid 338.58 g (1 mol) of erucic acid (purity 93%) were ozonized in analogy to Example 1, and then hydrogenation was carried out. The hydrogenation solution obtained in this way contained perlagonaldehyde and tridecanal acid. For oxidation, the corresponding aldehyde fraction was employed and was oxidized at 20 bar in analogy to Example 1. 132 g of perlagonic acid per cycle were obtained with a purity of 94%.

EXAMPLE 7

Pentadecanoic acid 224.4 9 (1 mol) of hexadecene (purity 95%) were ozonized in analogy to Example 1, and then hydrogenation was carried out to give pentadecanal.

The aldehyde was oxidized as in Example 1. After the end of the reaction, the autoclave was let down, the solvent was removed in vacuo and the residue was stirred in water with cooling. The pentadecanoic acid obtained in this way is separated off and dried.

Yield: 92%

Purity: 93%

In addition, the following products were prepared by the process of the invention:

| Ex. | Pre | P | P (bar) | T (°C.) | Y (%) | Pur (%) |
|---|---|---|---|---|---|---|
| 8 | 13-oxotridecanoic acid methyl ester | brassylic acid monomethyl ester | 14 | 64–90 | 92 | 95 |
| 9 | 2-ethylhexanal | 2-ethylhexanoic acid | 20 | 80 | 98 | 95 |
| 10 | 1,12-dimethoxy-1,12-dihydroxy-dodecane | dodecanedioic acid | 16 | 80–85 | 99 | 95 |
| 11 | 1,1,8,8-tetramethoxyoctane | octanedioic acid | 10 | 80–85 | 90 | 90 |
| 12 | heptanedialdehyde | heptanedioic acid | 15 | 80–85 | 97 | 90 |
| 13 | 9-oxononanoic acid methyl ester | azelaic acid monomethyl ester | 10 | 80–83 | 92 | 94 |
| 14 | benzaldehyde | benzoic acid | 12 | 80–85 | 98 | 98 |

The diluent employed was in each case acetic acid. The following abbreviations have been used:

| | |
|---|---|
| Pre | precursor for the oxidation |
| P | product obtained by oxidation |
| p | pressure |
| T | temperature |
| Y | yield |
| Pur | purity |

What we claim is:

1. A process for the preparation of aliphatic or aromatic mono- or dicarboxylic acids of 4 to 22 carbon atoms by oxidation of the corresponding aldehydes having the same number of carbon atoms, which consists essentially of carrying out the oxidation in a carboxylic acid selected from the group consisting of formic acid, acetic acid and propionic acid, or in a carboxylic acid/water mixture, at a temperature of 50°–130° C. and at a pressure of from 1 to 25 bar in the presence of an oxidizing agent.

2. The process as claimed in claim 2, wherein the aldehyde employed is an aliphatic or aromatic aldehyde having one or two aldehyde groups, hemiacetal or full acetal groups or mixtures thereof.

3. The process as claimed in claim 2, wherein a mixture of aldehyde and its full acetal and/or hemiacetal, in which the aldehyde content can be 1–99%, is employed.

4. The process as claimed in claim 1, wherein acetic acid is used as carboxylic acid.

5. The process as claimed in claim 1, wherein the oxidation is carried out in a carboxylic acid/water mixture with a water content of from 0.1 to 25% by volume.

6. The process as claimed in claim 1, wherein the oxidation is carried out at a temperature of from 60° to 90° C.

7. The process as claimed in claim 1, wherein the oxidation is carried out at from 8 to 25 bar.

8. The process as claimed in claim 1, wherein oxygen is used as oxidizing agent.

9. A process for the preparation of aliphatic or aromatic mono- or dicarboxylic acids of 4 to 22 carbon atoms by oxidation of the corresponding aldehydes having the same number of carbon atoms, which comprises carrying out the oxidation in a carboxylic acid from the group consisting of formic acid, acetic acid and propionic acid, or in a carboxylic acid/water mixture, at a temperature of 50°–130° C. and at from 1 to 25 bar in the presence of an oxidizing agent, wherein the oxidation is carried out in the absence of a catalyst.

10. A process for the preparation of aliphatic or aromatic mono- or dicarboxylic acids of 4 to 22 carbon atoms by oxidation of the corresponding aldehydes having the same number of carbon atoms, which comprises carrying out the oxidation in a carboxylic acid form the group consisting of formic acid, acetic acid and propionic acid, or in a carboxylic acid/water mixture, at a temperature of 50°–130° C. and at from 1 to 25 bar in the presence of an oxidizing agent, wherein the oxidation is carried out in the absence of a catalyst and an aprotic solvent.

11. A process for the preparation of aliphatic or aromatic mono- or dicarboxylic acids of 4–22 carbon atoms, which comprises reacting a chemical compound having at least one olefinic double bond with ozone in the presence of a solvent, catalytically hydrogenating the resulting peroxide solution, and then oxidizing the resulting aldehyde, after separating off the solvent and the catalyst, in the presence of a carboxylic acid from the group consisting of acetic acid, formic acid and propionic acid, or of a carboxylic acid/water mixture, at 50°–130° C. and 1–25 bar, in the presence of an oxidizing agent, to give the desired mono- or dicarboxylic acid, wherein the oxidation is carried out in the absence of a catalyst and an aprotic solvent.

* * * * *